(12) United States Patent
Heydrich et al.

(10) Patent No.: US 7,211,698 B2
(45) Date of Patent: May 1, 2007

(54) METHOD FOR PROCESSING COMPOSITIONS CONTAINING 1,1,2,2-TETRAMETHOXYETHANE AND GLYOXAL DIMETHYL ACETAL

(75) Inventors: Gunnar Heydrich, Limburgerhof (DE); Ingo Richter, Mannheim (DE); Thomas Krug, Worms (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/570,804

(22) PCT Filed: Sep. 3, 2004

(86) PCT No.: PCT/EP2004/009832

§ 371 (c)(1),
(2), (4) Date: Mar. 6, 2006

(87) PCT Pub. No.: WO2005/023743

PCT Pub. Date: Mar. 17, 2005

(65) Prior Publication Data

US 2006/0264678 A1  Nov. 23, 2006

(30) Foreign Application Priority Data

Sep. 4, 2003  (DE) ................. 103 40 738

(51) Int. Cl.
C07C 41/58 (2006.01)
(52) U.S. Cl. ...................... 568/600; 568/603
(58) Field of Classification Search ........... 568/600, 568/603
See application file for complete search history.

(56) References Cited

U.S. PATENT DOCUMENTS 2,360,959 A * 10/1944 MacDowell et al.
5,426,239 A * 6/1995 Dressaire et al.
5,914,012 A * 6/1999 Kaibel et al.
6,013,842 A * 1/2000 Gröning et al.
6,713,656 B2 * 3/2004 Heydrich et al.

FOREIGN PATENT DOCUMENTS

| | | | |
|---|---|---|---|
| DE | 102 09 195 A1 | * | 9/2003 |
| EP | 0 607 722 B1 | * | 7/1994 |
| EP | 0 804 951 A2 | * | 11/1997 |
| EP | 0 847 976 A1 | * | 6/1998 |
| EP | 1 300 383 A2 | * | 4/2003 |
| GB | 359362 | * | 3/1931 |

OTHER PUBLICATIONS

"Gloyoxal Derivatives. V. Reaction of Alcohols with Glyoxal" J.M. Kliegman et al. *J. Org. Chem.*, vol. 38, No. 3 (1973) pp. 556-560, no month provided.*

"The Monoacetalization of Glyoxal: A Direct Synthesis of 2,2-Dimethoxy and Diethoxy Ethanals" Chastrette et al., *Synthetic Communications*, 1988, pp. 1343-1348, no month provided.*

* cited by examiner

*Primary Examiner*—Rosalynd Keys
(74) *Attorney, Agent, or Firm*—Connolly, Bove, Lodge & Hutz, LLP (57) ABSTRACT

A process is proposed for distillatively working up an aqueous composition which comprises 1,1,2,2-tetramethoxyethane, glyoxal dimethyl acetal and methanol, wherein the workup of this composition is carried out in a dividing wall column to form low boiler, medium boiler and/or high boiler fractions, and a dividing wall is disposed in the longitudinal direction in the dividing wall column to form an upper common column region, a lower common column region, a feed section having rectifying section and stripping section and a withdrawal section having stripping section and rectifying section, and the aqueous composition is fed into the middle region of the feed section.

21 Claims, 2 Drawing Sheets

METHOD FOR PROCESSING COMPOSITIONS CONTAINING 1,1,2,2-TETRAMETHOXYETHANE AND GLYOXAL DIMETHYL ACETAL

This application is a National Stage of PCT/EP2004/009832 filed Sep. 3, 2004 which in turn claims priority from German Application 103 40 738.3, filed Sep. 4, 2003.

DESCRIPTION

The present invention relates to a process for distillatively working up an aqueous composition which comprises 1,1,2,2-tetramethoxyethane, glyoxal dimethyl acetal and methanol. These aqueous compositions are generally obtained as the reaction effluent in processes for preparing mono- or diacetals of glyoxal.

Monoacetals (e.g. glyoxal dimethyl acetal) and diacetals of glyoxal (e.g. 1,1,2,2-tetra-methoxyethane) are important intermediates in organic synthesis.

It is common knowledge that mono- or diacetals of glyoxal can be prepared in an equilibrium reaction by acid-catalyzed acetalization of glyoxal with monohydric alcohols R—OH: the acid-catalyzed acetalization of glyoxal with monohydric alcohols is a complex reaction in which not only the monoacetal and the diacetal, but also a multitude of oligomers and/or cyclic by-products may be formed (see, for example, J. M. Kliegmann et al. in J. Org. Chem., Vol. 38 (1973), p. 556).

The reaction of glyoxal with water-miscible alcohols, as described, for example, in U.S. Pat. No. 2,360,959, usually affords low yields of diacetal. In order to increase the yield of diacetal, water has to be removed continuously from the reaction mixture in order to appropriately shift the equilibrium of the reaction. This removal is difficult to perform, especially in the case of water-miscible alcohols. For this purpose, GB 359 362 recommends the use of an inert solvent as an azeotroping agent for removing water from the reaction mixture. The selection of a suitable azeotroping agent is based on its boiling point and its boiling behavior in the reaction mixture. However, the use of azeotroping agents leads to additional costs.

In Synth. Comm. 1988, 18, pages 1343 to 1348, Chastrette et al. describe the acetalization of glyoxal in chloroform. The catalyst used in order to obtain high yields of diacetal in a prolonged reaction time is zirconium sulfate. In addition, the solvent and azeotroping agent used is chloroform which is damaging to health, but leads to the additional costs which have already been mentioned.

In order to obtain glyoxal mono- or diacetals in good yields from the reaction effluent of the reaction of glyoxal with alcohols, the prior art describes multistage and complex separating processes.

EP 0 607 722 describes a process in which the distillative workup is carried out in at least 5 columns and additionally at different pressure levels, in order to obtain an aqueous glyoxal dimethyl acetal solution. In a first column, the majority of the excess alcohol is removed at atmospheric pressure (step 1). Subsequently, an aqueous mixture which comprises the majority of the glyoxal acetals is prepared in a second column (step 2). After distillative isolation in a third column, the diacetal is obtained from this mixture as an aqueous azeotrope (step 3) and fed to an additional reactor in which it is dissociated back to glyoxal and methanol. After the alcohol has been removed from this solution in a fourth column (step 5), the glyoxal is fed back to the reactor after the glyoxal concentration has been increased to 70% in a further fifth column (step 6). The bottom product obtained during this distillation comprises the monoacetal and can be concentrated to the desired concentration in a further apparatus (step 4).

EP 0 847 976 A1 describes a multistage distillative workup of a similar effluent in which the excess alcohol is first removed (step 1), then the diacetal is obtained with the addition of water as an aqueous homoazeotrope (step 2) and this is isolated by an azeotroping agent distillation (step 5) and recycled into the process. The monoacetal is subsequently obtained by a steam distillation and a subsequent fractional distillation (steps 3 and 4) and the resulting distillation residues are recycled.

In addition, it is common to the two latter processes that the reactants used are concentrated glyoxal solutions, since commercial glyoxal solutions only have a glyoxal content of about 40% and their use results in lower yields being achieved. Methods for concentrating this solution are known and are described, for example, in EP 1 300 383 A2. However, additional apparatus is required to concentrate the commercial glyoxal solutions.

The prior art processes thus imply complex plants, internals whose acquisition has high capital costs and a high energy requirement.

It is an object of the present invention to provide a process for working up aqueous compositions which comprise 1,1,2,2-tetramethoxyethane, glyoxal dimethyl acetal and methanol, which can afford the corresponding pure products by suitable process configuration with apparatus of low complexity.

We have found that this object is achieved by a process for distillatively working up an aqueous composition which comprises 1,1,2,2-tetramethoxyethane, glyoxal dimethyl acetal and methanol.

In the process according to the invention, the composition is worked up to form at least one low boiler fraction, at least one medium boiler fraction and at least one high boiler fraction in a dividing wall column in which a dividing wall is arranged in the longitudinal direction of the column to form an upper common column region, a lower common column region, a feed section having rectifying section and stripping section and a withdrawal section having rectifying section and stripping section, the dividing wall is arranged between the upper and the lower common column region and the aqueous composition is fed to the middle region of the feed section, and at least one medium boiler fraction comprising aqueous 1,1,2,2-tetramethoxyethane is obtained as a sidestream from the middle region of the withdrawal section, at least one high boiler fraction comprising glyoxal dimethyl acetal from the lower common column region and at least one low boiler fraction comprising methanol from the upper common column region.

Aqueous Composition

The aqueous composition employed in the process according to the invention preferably has one or more of the following contents whose sum does not exceed 100% by weight:

from 8 to 28% by weight of 1,1,2,2-tetramethoxyethane, from 2 to 12% by weight of glyoxal dimethyl acetal, from 40 to 80% by weight of methanol and from 5 to 18% by weight of water.

When 1,1,2,2-tetramethoxyethane is to be obtained from the aqueous composition by the process according to the invention, the aqueous composition employed in the process according to the invention preferably has one or more of the following contents whose sum does not exceed 100% by weight:

from 12 to 16% by weight of 1,1,2,2-tetramethoxyethane,
from 2 to 8% by weight of glyoxal dimethyl acetal,
from 60 to 80% by weight of methanol and
from 5 to 12% by weight of water.

In a preferred embodiment of the present invention, the aqueous composition which is employed in the process according to the invention additionally contains from 0 to 4% by weight of glyoxal.

The aqueous composition employed in the process according to the invention may additionally comprise further compounds which are selected from the group consisting of 2,3-dimethoxy-1,4-dioxane and 2-(dimethoxymethyl)-1,3-dioxolane.

When 2,3-dimethoxy-1,4-dioxane is present in the aqueous composition, its content in the aqueous composition is preferably from 0 to 10% by weight, more preferably from 0 to 5% by weight. When 2-(dimethoxymethyl)-1,3-dioxolane is present in the aqueous composition, its content in the aqueous composition is preferably from 0 to 8% by weight, more preferably from 0 to 4% by weight.

In a preferred embodiment, the aqueous composition which is used in the process according to the invention is prepared by processes which are described in EP 1 300 383 A2 or EP 0 847 976 A1, whose disclosure contents are fully incorporated by reference into the present patent application.

The process of EP 1 300 383 A2 serves to prepare diacetals of glyoxal. The process comprises the reaction of from 40 to 75% by weight aqueous glyoxal with methanol in the presence of an acidic catalyst. This involves contacting a liquid mixture which, at the start of the reaction, contains methanol and glyoxal in a molar ratio of at least 15:1 and water in a concentration of not more than 8% by weight with the acidic catalyst until the concentration of the 1,1,2,2-tetramethoxyethane formed In the reaction mixture has reached at least 70% of the equilibrium concentration. Not more than 5% by weight of the methanol is distilled off at the same time or beforehand. The reaction effluents resulting from this process comprise at least 1,1,2,2-tetramethoxyethane, glyoxal dimethyl acetal, water and methanol. Before the reaction, the aqueous glyoxal is preferably brought by dewatering to a content of from 60 to 75% by weight of glyoxal. This results in better yields being obtained in the acetalization. The dewatering is preferably effected under a reduced pressure of from 100 to 200 mbar.

In a further preferred embodiment, the aqueous composition which is employed in the process according to the invention is obtained in a process according to EP 0 847 976 A1. In this process, glyoxal monoacetals of the general formula (I)

(I)

are prepared by reacting a mixture of glyoxal and glyoxal bisacetals of the general formula (II)

(II)

in the presence of an acidic catalyst with an excess of a monohydric alcohol R—OH until the reaction equilibrium has been attained. The glyoxal solution used in this preparation is preferably in the form of an aqueous solution, and it is appropriate to use the customary technical aqueous solutions having a glyoxal content of from 20 to 60% by weight, preferably from 30 to 50% by weight. However, before it is reacted, the aqueous glyoxal solution may also be brought by dewatering to a content of from 60 to 75% by weight, preferably from 65 to 70% by weight.

The R radical of the formulae I and II is derived directly from the alcohol of the general formula ROH used and is thus the same. R is branched or unbranched $C_1$–$C_4$–alkyl and/or branched or unbranched $C_2$–$C_4$–alkenyl. $C_1$–$C_4$–Alkyl is, for example, methyl, ethyl, propyl, isopropyl and butyl. $C_2$–$C_4$–Alkenyl is, for example, vinyl, propenyl and isopropenyl. Particularly preferred R radicals are methyl and ethyl.

Dividing Wall Column

For the continuous distillative separation of multisubstance mixtures, various process variants can be used. In the simplest case, the feed mixture is separated into two fractions, a low-boiling top fraction and a high-boiling bottom fraction. In the separation of feed mixtures into more than two fractions, a plurality of distillation columns has to be used in this process variant. In order to reduce the apparatus demands, columns having liquid or vaporous sidestreams are used if possible in the separation of multisubstance mixtures. However, the possibility of employing distillation columns having sidestreams is highly restricted in that the products removed at the sidestream takeoff points are never completely pure. In the case of side withdrawals in the rectifying section, which are typically in liquid form, the side product still contains fractions of low-boiling components which are to be removed via the top. The same applies for side withdrawals in the stripping section which are usually in vaporous form and in which the side product still contains high boiler fractions. The use of conventional sidestream columns is therefore restricted to cases in which contaminated side products are permissible.

A means of remedy is offered by what are known as dividing wall columns which are described, for example, in EP-A 0 122 367. Dividing wall columns are distillation columns having vertical dividing walls which prevent transverse mixing of liquid and vapor streams in subregions. The dividing wall which preferably consists of a metal sheet divides the column in the longitudinal direction in its middle region into a feed section and into a withdrawal section.

The dividing wall column used in the process according to the invention thus has a dividing wall which is aligned in the longitudinal direction of the column and divides the column interior into the following subregions: an upper common column region, a lower common column region and a feed section and a withdrawal section, each having rectifying section and stripping section. The mixture to be separated is introduced in the region of the feed section, and at least one high boiler fraction is withdrawn from the column bottom, at least one low boiler fraction via the column top and a medium boiler fraction from the region of the withdrawal section. With regard to the arrangement of the regions in the dividing wall column, reference is made to DE 101 00 552 A1, whose disclosure content is hereby incorporated by reference into the present patent application.

In the dividing wall column used in the process according to the invention, it is preferred that the upper common subregion has from 5 to 50%, preferably from 15 to 30%, of the total number of theoretical plates of the dividing wall column, the rectifying section of the feed section has from 5 to 50%, preferably from 15 to 30%, of the total number of theoretical plates of the dividing wall column, the stripping section of the feed section has from 5 to 50%, preferably from 15 to 30%, of the total number of theoretical plates of the dividing wall column, the stripping section of the withdrawal section has from 5 to 50%, preferably from 15 to 30%, of the total number of theoretical plates of the dividing wall column, the rectifying section of the withdrawal section has from 5 to 50%, preferably from 15 to 30%, of the total number of theoretical plates of the dividing wall column, and the lower common section has from 5 to 50%, preferably from 15 to 30%, of the total number of theoretical plates of the dividing wall column, the total number of theoretical dividing wall plates of the dividing wall column being 100%. It is thus preferably ensured that the theoretical plates of the dividing wall column are divided between the individual column regions in such a way that each has from 5 to 50% of the total number of theoretical plates of the dividing wall column. The feed section and the withdrawal section form the middle region of the dividing wall column.

The dividing wall column used in the process according to the invention preferably has from 30 to 120, more preferably from 50 to 100, most preferably from 60 to 80, theoretical plates.

The operating pressure of the dividing wall column in the process according to the invention is preferably from 300 to 1500 mbar, more preferably from 400 to 600 mbar.

In the dividing wall column used in the process according to the invention, the sum of the number of theoretical plates in the stripping and rectifying section in the feed section is preferably from 80 to 110%, more preferably from 90 to 100%, of the sum of the number of plates in the stripping and rectifying section in the withdrawal section.

The dividing wall column may be equipped in the stripping and/or rectifying sections of the feed and/or withdrawal section or in parts thereof with structured packings or random packings. In addition, it is possible that the dividing wall is configured with heat insulation in these subregions.

It is also possible to configure the dividing wall in the form of loosely inserted and adequately sealed subsegments. In this case, the dividing wall is not welded into the column. This leads to a further reduction in costs in the production and construction of dividing wall columns.

Particularly advantageously, the loose dividing wall may have internal manholes or removable segments which allow access within the dividing wall column from one side of the dividing wall to the other side.

With regard to the separating internals which can be used in the dividing wall column, there are in principle no restrictions: both random packings and structured packings or trays are suitable for this purpose. For reasons of cost, trays, preferably valve or sieve trays, are generally used in columns having a diameter above 1.2 meters. When the aqueous composition is worked up, it is recommended, especially in the dividing wall region and in the common upper column region, to use structured packings as internals. In this case, structured sheet metal or fabric packings having a specific surface area of preferably from 100 to 1000 $m^2/m^3$, more preferably from about 250 to 500 $m^2/m^3$, are particularly suitable. In the lower common subregion of the dividing wall column, trays may also be used with preference, more preferably valve trays.

In the event of particularly high requirements on the product purity, it is favorable, especially in the case that structured packings are used as separating internals, to provide the dividing wall with thermal insulation. Such a configuration of the dividing wall is described, for example, in EP 0 640 367. A double-walled configuration with a narrow gas space in between is particularly favorable.

The position of the dividing wall in the individual subregions of the dividing wall column is preferably adjusted in such a way that the cross sections of feed and withdrawal section have different surface areas.

In the process according to the invention, the aqueous composition, as a feed stream to the dividing wall column, is preferably partly or fully pre-evaporated in a pre-evaporator and fed to the column in biphasic form or in the form of a gaseous and a liquid stream.

In this case, the feed point and the sidestream takeoff point of the dividing wall column, with respect to the position of the theoretical dividing wall plates, are preferably disposed at different heights in the column, so that the feed point is disposed from 1 to 20, more preferably from 5 to 10, theoretical plates higher or lower than the sidestream takeoff point. However, the feed point and the sidestream takeoff point may also be at the same height.

The liquid distribution in the individual subregions of the column is preferably deliberately nonuniform. In such a process variant, the liquid distribution in the individual subregions of the dividing wall column can preferably in each case be adjusted separately. This allows the total energy amount which is required to separate the aqueous composition to be minimized.

Particularly advantageously, the liquid may be introduced to an increased extent in the wall region in the rectifying sections of the dividing wall column and to a reduced extent in the wall region in the stripping sections of the dividing wall column. This prevents undesired creep streams and increases the achievable end product purities.

In addition to a top and a bottom product, side products may likewise be obtained in pure form from dividing wall columns. When multisubstance mixtures are separated into a low boiler, a medium boiler and a high boiler fraction, specifications of the maximum permissible level of low and high boilers in the medium boiler fraction are customarily made. In this context, specifications are made for components which are critical to the separation problem, known as key components. These may be individual key components or the sum of a variety of key components. In the present process, methanol (low boilers) and glyoxal dimethyl acetal and 2,3-dimethoxy-1,4-dioxane (high boilers), when present in the column feed, are key components.

In a preferred process variant, it is ensured that the abovementioned specifications with regard to the key components are complied with by controlling the division ratio of the liquid at the upper end of the dividing wall and also the heating output of the evaporator in a defined manner. The division ratio of the liquid at the upper end of the dividing wall is adjusted in such a way that the proportion of high-boiling key components in the liquid reflux via the stripping section of the withdrawal section is from 10 to 80%, preferably from 30 to 50%, of the limiting value permissible in the medium boiler fraction. The heating output in the bottom evaporator of the dividing wall column is preferably adjusted in such a way that the concentration of low-boiling key components in the liquid at the lower end of the dividing wall is from 10 to 80%, preferably from 30 to 50%, of the limiting value permissible in the medium boiler stream. In accordance with this control, the liquid division at the upper end of the dividing wall is adjusted to the effect that when the contents of high-boiling key components are higher, more liquid is passed to the feed section, and when the contents thereof are lower, less liquid is passed to the feed section.

The heating output in the evaporator is preferably adjusted in such a way that the concentration of those components in the low boiler fraction for which a certain limiting value for the concentration is to be attained in the sidestream (key components) is adjusted at the lower end of the dividing wall in such a way that the concentration of components of the low boiler fraction in the liquid at the lower end of the dividing wall makes up from 10 to 80%, preferably from 30 to 50%, of the value which is to be attained in the sidestream product, and the heating output is adjusted to the effect that when the content of components of the low boiler fraction is higher, the heating output is increased, and when the content of components of the low boiler fraction is lower, the heating output is reduced.

To compensate for disruptions in the feed rate or the feed concentration, it is additionally found to be advantageous to use appropriate control methods in the process control system to ensure that the flow rates of the liquids which are introduced to the rectifying sections can never fall below 30% of their normal value.

In a preferred process variant, the vapor stream at the lower end of the dividing wall may be adjusted in such a way that the ratio of vapor stream in the feed section to the vapor stream in the withdrawal section is from 0.5 to 2, preferably from 0.9 to 1.1. This is preferably effected by the selection and/or dimensioning of separating internals and/or the incorporation of internals which cause a pressure drop, for example of perforated plates.

Suitable for withdrawing and dividing the liquids at the upper end of the dividing wall and at the side withdrawal point are collection chambers for the liquid which are mounted either inside or outside the column and assume the function of a pump reservoir or ensure a sufficiently high static liquid head, which enable controlled further flow of liquid using control units, for example valves. When packed columns are used, preference is given to initially capturing the liquid in collectors and passing it from there into an internal or external collecting chamber.

In a further embodiment of the present invention, the liquid leaving the upper common section of the column is collected in a collecting chamber disposed in the column or outside the column and separated at the upper end of the dividing wall in a controlled manner by a fixed setting or closed-loop control in such a way that the ratio of liquid stream in the feed section to that of the withdrawal section is from 0.1 to 1.0, preferably from 0.2 to 0.5.

In this case, the liquid is conveyed to the feed section, preferably using a pump, or introduced with flow rate control using a static feed head of at least one meter. This is preferably effected by cascade closed-loop control in conjunction with the closed-loop liquid level control in the collecting chamber.

The liquid leaving the stripping section in the withdrawal section of the column is preferably divided between the sidestream and the rectifying section of the column by closed-loop control, in such a way that the amount of liquid introduced to the rectifying section cannot fall below 30% of the normal value.

Preference is given to obtaining at least one high boiler fraction as liquid sidestream in the lower section of the column, more preferably from 1 to 5 theoretical plates above the column bottom. This high boiler fraction comprises glyoxal dimethyl acetal which, for the preferred preparation of 1,1,2,2-tetramethoxyethane, may optionally be recycled into the preparation of the aqueous composition which is preferably effected in accordance with EP 0 847 976 A1 or EP 1 300 383 A2.

In a preferred embodiment of the process according to the invention, the high boiler fraction may thus be reused at least partly to prepare the aqueous composition. Alternatively, it is also possible, before the recycling, to further work up the high boiler fraction which still contains a relatively large proportion of glyoxal dimethyl acetal, in order to obtain pure, aqueous glyoxal dimethyl acetal solution. This makes it possible to prepare glyoxal dimethyl acetal.

Preference is further given to recycling the column bottoms, i.e. not the output from 1 to 5 theoretical plates above the column bottom, into the bottom evaporator.

The bottom product is preferably withdrawn under closed-loop temperature control, and the control temperature used is measured at a point in the lower common subregion of the column. This measurement point is preferably disposed from 3 to 8, more preferably from 4 to 6, theoretical plates above the lower end of the column. The withdrawal of the bottom product under closed-loop temperature control is a standard closed-loop control method for columns which is known to those skilled in the art: when the temperature goes below a certain temperature in the bottoms, less bottom product is removed, which causes the fill level to rise and more side product to be removed. Consequently, the medium boilers move upward from the bottoms.

Preference is given to obtaining glyoxal dimethyl acetal from the high boiler takeoff of the dividing wall column.

The medium boiler fraction is preferably withdrawn in liquid form at the sidestream takeoff point. However, it is additionally also possible that the medium boiler fraction is removed in gaseous form at the sidestream takeoff point.

The medium boiler fraction is preferably withdrawn at the sidestream takeoff point under closed-loop level control, and the control parameter used is the liquid level in the column bottom. In the process according to the invention, the medium boiler fraction comprises, in addition to water, 1,1,2,2-tetramethoxyethane. If glyoxal dimethyl acetal is to be obtained by the process according to the invention, this medium boiler fraction may preferably be continuously contacted with an acidic ion exchanger to dissociate the 1,1,2,2-tetramethoxyethane and recycled into the dividing wall column, preferably into the evaporator which is optionally connected upstream, or else used for the reactions according to EP 0 847 976 A1 or EP 1 300 383 A2, for example by feeding into the dewaterings upstream of the reactions.

The distillate is also preferably withdrawn under closed-loop temperature control, and the control temperature used is preferably measured at a point in the upper subregion of the column which is disposed from 3 to 10, more preferably from 4 to 6, theoretical plates below the upper end of the column. The distillate comprises methanol.

In a preferred embodiment of the process according to the invention, the methanolic distillate obtained at the top of the dividing wall column is either recycled into the dividing wall column or reused to prepare the aqueous composition.

At the upper and at the lower end of the dividing wall column, the dividing wall column used in the process according to the invention preferably has sample-taking means, through which liquid and/or gaseous samples can be withdrawal from the column, continuously or at time intervals, and be investigated with regard to their composition, preferably by gas chromatography.

The present invention further relates to the use of dividing wall columns to distillatively work up an aqueous composition which comprises 1,1,2,2-tetramethoxyethane, glyoxal dimethyl acetal and methanol.

Two Thermally Coupled Columns

According to the invention, it is also possible to use thermally coupled columns instead of the dividing Wall columns. Arrangements having thermally coupled columns are equivalent to a dividing wall column with regard to the energy demand. This inventive variant is relevant especially when existing columns are available, since this avoids new high capital costs. The suitable forms of the arrangement may be selected depending on the number of plates of the columns present.

The present invention thus further provides a process for distillatively working up an aqueous composition which comprises 1,1,2,2-tetramethoxyethane, glyoxal dimethyl acetal and methanol, which comprises carrying out the workup of the composition in a combination of two distillation columns in the form of a thermal coupling.

The process features which have been listed above for the dividing wall column also apply correspondingly to the embodiment having two thermally coupled columns. This also applies to the aqueous composition used in the process according to the invention.

The thermally coupled columns may each be provided with a dedicated evaporator and/or condenser. In a preferred process variant, only liquids are conveyed in the connecting streams between the two thermally coupled columns. This is particularly advantageous when the thermally coupled columns are operated with different pressures.

In a preferred connection of the thermally coupled columns, the low boiler fraction and the high boiler fraction are withdrawn from different columns, and the operating pressure of the column from which the high boiler fraction is withdrawn is set lower than the operating pressure of the column from which the low boiler fraction is withdrawn, preferably by from 0.5 to 1 bar.

The first column is preferably operated at a pressure of from 500 to 1500 mbar, more preferably from 800 to 1200 mbar. The temperature in the first column is preferably from 45 to 115° C., more preferably from 55 to 105° C. The second column is preferably operated at a pressure of from 50 to 500 mbar, more preferably from 100 to 200 mbar. The temperature in the second column is preferably from 30 to 105° C., more preferably from 45 to 95° C.

In a particular form of connection, it is possible to partly or fully evaporate the bottom stream of the first column in an evaporator and subsequently to feed it to the second column in biphasic form or in the form of a gaseous or of a liquid stream. In addition, it may be advantageous to subject the feed stream to a pre-evaporation and subsequently to feed it to the column in biphasic form or in the form of two streams. This pre-evaporation is particularly relevant when the feed stream contains relatively large amounts of low boilers. The pre-evaporation also allows the stripping section of the column to be significantly deburdened. The same also applies for the abovementioned pre-evaporation in dividing wall columns.

In the variant having thermally coupled columns, the sample-taking means, preferably similarly to the embodiment with the dividing wall column, are disposed in the connecting lines between the regions of the thermally coupled columns corresponding to the subregions of the dividing wall column.

The present invention further provides the use of two thermally coupled columns for distillatively working up an aqueous composition which comprises 1,1,2,2-tetramethoxyethane, glyoxal dimethyl acetal and methanol. With regard to continuing procedure, reference is made to the process outlined above.

Dividing Wall Column or Two Thermally Coupled Columns

In the process according to the invention, preference is given to feeding water into the feed of the dividing wall column or of the second thermally coupled column, so that a diacetal concentration in the bottom of the dividing wall column or of the second thermally coupled column of less than 5% by weight, preferably less than 1% by weight, is established. This is advantageous in order to achieve substantially complete diacetal removal. It is useful in this context that, as described in EP 0 847 976 A1, 1,1,2,2-tetramethoxyethane and water form a homoazeotrope. In a further preferred embodiment, the water is fed into the bottom evaporator feed of the dividing wall column or of the second thermally coupled column. This added water may preferably be removed at least partly from the water stream which is obtained in the evaporation of the glyoxal which preferably takes place before the reaction according to EP 1 300 383 A2 or EP 0 847 976 A1. Alternatively, the water obtained in the purifying distillation of the 1,1,2,2-tetramethoxyethane which is downstream of the dividing wall column or of the two thermally coupled columns may also be used.

Furthermore, in a preferred embodiment of the process according to the invention, commercial, about 40% glyoxal solution is fed into the feed of the dividing wall column or of the second thermally coupled column. This may appropriately be effected via the bottom evaporator feed.

Both in the embodiment with the dividing wall column and in the embodiment with the thermally coupled columns, the bottom evaporator is preferably a thin-film apparatus, preferably a falling-film evaporator.

The liquid or gaseous aqueous side effluent which is obtainable from the withdrawal section of the dividing wall column or from the side effluent of the second thermally coupled column and comprises 1,1,2,2-tetramethoxyethane is subsequently preferably fed into a further column which is equipped with trays, structured packings or random packings, in which the water is removed with the aid of an azeotroping agent distillation. This column preferably has from 10 to 40, more preferably from 10 to 25, theoretical plates.

The azeotroping agent used is preferably selected from $C_5$ to $C_{10}$ hydrocarbons. The 1,1,2,2-tetramethoxyethane is obtained from this second column preferably at least partly as a liquid or gaseous sidestream in the lower section of the column, preferably from 1 to 5 theoretical plates above the column bottom. This distillation takes place at pressures of preferably from 300 to 1500 mbar, more preferably from 400 to 600 mbar. In a preferred embodiment of the present invention, the aqueous side effluent of the dividing wall column or of the second thermally coupled column is introduced substantially in gaseous form into the azeotroping agent distillation column, which is a particularly energy-saving procedure. In this case, the operating pressure selected for the azeotroping agent distillation column will be lower than that of the dividing wall column or of the second thermally coupled column, preferably by from 10 to 50 mbar. Suitable control units which are known to those skilled in the art will preferably be incorporated into the connecting line between the columns, for example a flap and a diaphragm having appropriate differential pressure measurement, which allow the above-described closed-loop control of the sidestream takeoff rate.

The bottom effluent of this azeotroping agent column is preferably fed to the feed point of the dividing wall column. This may be effected, for example, by feeding into the reactor effluent or into the preheated or semievaporated column feed.

The 1,1,2,2-tetramethoxyethane obtained in this way has a water content of preferably less than 1%, more preferably less than 0.1%.

In a further particular embodiment of the present invention, the wastewater obtained at the top of this further column is contacted continuously with an acidic ion exchanger. The residence time on the ion exchanger is preferably from 1 to 4 hours at a temperature of from 55 to 100° C., preferably from 55 to 80° C.

The invention is illustrated in detail hereinbelow with the aid of the drawings and also of an inventive example.

Figure 1:
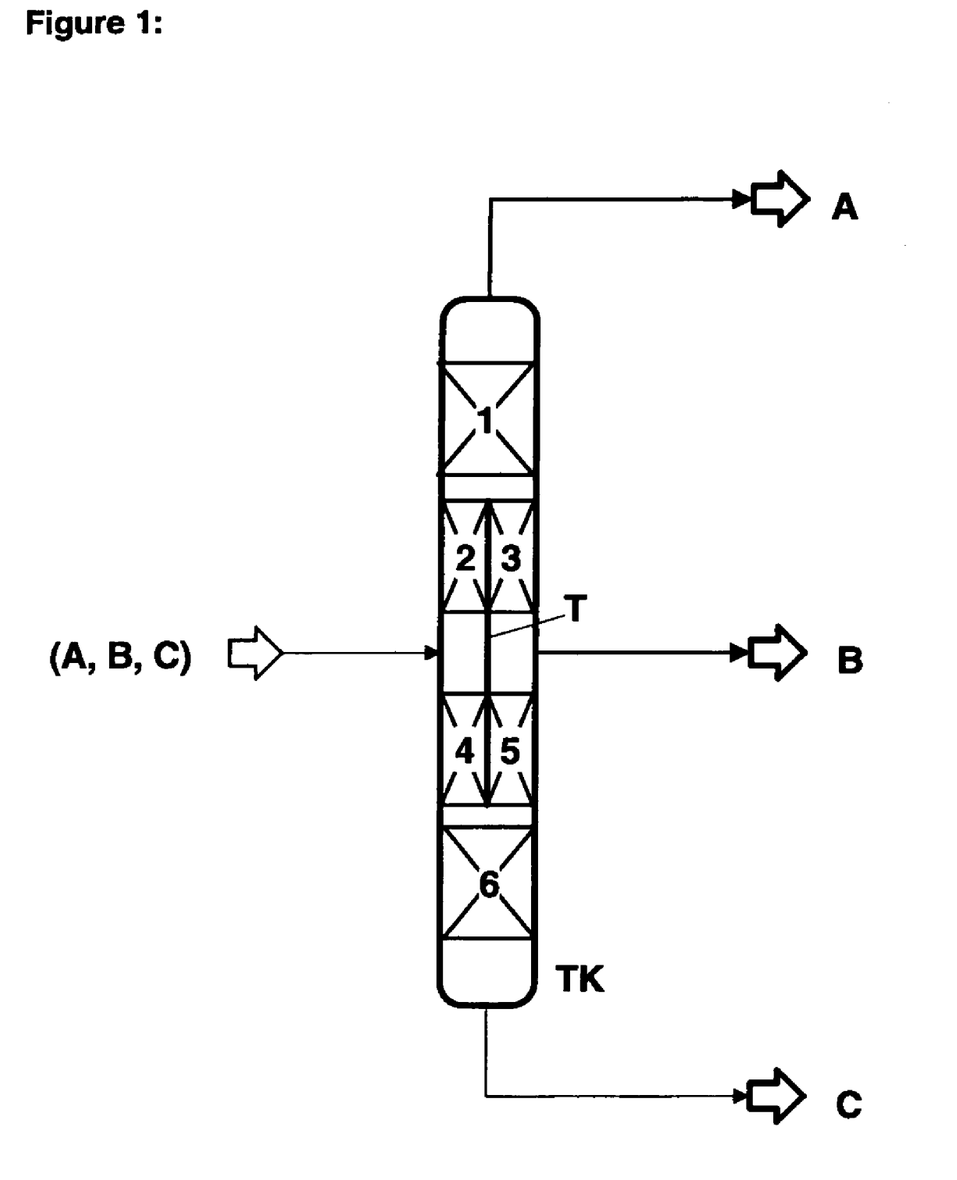
FIG. 1 shows a schematic of a dividing wall column (TK) with dividing wall (T) which is disposed vertically therein and divides the column into an upper common column section 1, into a lower common column section 6, a feed section (2, 4) having rectifying section 2 and stripping section 4, and also a withdrawal section (3, 5) with stripping section 3 and rectifying section 5. The mixture to be separated (A B C) is fed in the middle region of the feed section (2, 4). At the top of the column, the low boiler fraction (A) is removed, the high boiler fraction (C) is removed from the column bottom and the medium boiler fraction (B) is removed from the middle region of the withdrawal section (3, 5).
Figure 2:
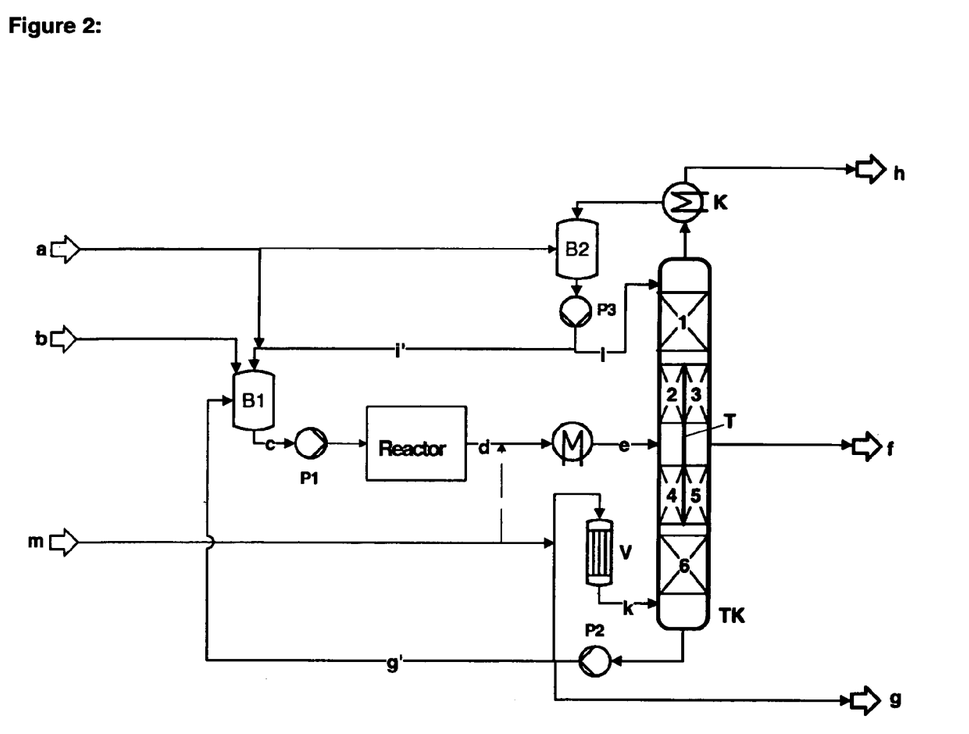
FIG. 2 shows the schematic illustration of a plant for distillatively working up the aqueous composition for preparing 1,1,2,2-tetramethoxyethane and/or glyoxal dimethyl acetal in a dividing wall column.

The separation of the reaction effluent d into methanolic low boiler fractions i and i', the aqueous diacetal f and high boiler fraction g and g' which, in addition to other components, comprises the glyoxal dimethyl acetal and unconverted glyoxal will now be illustrated. In the workup of the aqueous composition, the high boiler fraction may for the most part be recycled directly into the synthesis stage (stream g') which not only gives a distinct improvement in yield but is also a particularly environmentally friendly and resource-protective procedure.

The aqueous composition, stream d, is partly evaporated in a pre-evaporator to obtain a biphasic stream e which is fed to the dividing wall column (TK).

The dividing wall column (TK) is divided by the dividing wall (T) disposed in the longitudinal direction into the subregions 1 to 6, i.e. into the upper common column region 1, the feed section having rectifying section 2 and stripping section 4, the withdrawal section having rectifying section 5 and stripping section 3, and also the lower common column region 6.

The aqueous 1,1,2,2-tetramethoxyethane is removed as stream f as a side effluent (liquid or gaseous). The high boiler discharge or recycling is effected via streams g and g'. The low boiler discharge or recycling is effected via the streams i, i'.

It addition, water or aqueous glyoxal solution is introduced into the dividing wall column via stream m or k via the evaporator effluent.

Further definitions in FIG. 2 are: a methanol, b glyoxal solution, c reactive feed, B1 stirred vessel to store the reactive mixture, B2 vessel to store stream a and top effluent i', P1, P2, P3 pumps with closed-loop flow control, V evaporator, k evaporator effluent and h condenser output.

IMPLEMENTATION EXAMPLE

Construction of the Laboratory Apparatus According to FIG. 2 for Acetalizing Glyoxal A stirred vessel B1 having a capacity of about 0.5 l is initially charged with the reaction mixture and metered continuously (stream c) with a pump under closed-loop flow control (130g/h) into the reactor heated to 65° C. This tubular reactor consists of a jacket-heated stainless steel tube of length 10 meters which has been charged with 620 ml of catalyst (LEWATIT® K2629). The fine filters having a mesh width of 140 µm which are mounted at the inlet and outlet of the reactor prevent the discharge of the catalyst. The effluent of this reactor d is conducted via a line into the feed point of the dividing wall column.

A pressure-retaining valve in this line ensures a constant operating pressure in the reactor of about 0.5 bar above atmospheric pressure.

The dividing wall column is operated at a pressure of 500 mbar (absolute). The dividing wall column TK used is a glass laboratory column of internal diameter 50 mm which is provided in the region of the dividing wall with a bed of 3 mm stainless steel mesh rings which is about 80 cm in height. Above the dividing wall in the common column region 1, the column is equipped with 50 cm of a laboratory fabric packing having a specific surface area of about 950 $m^2/m^3$. Below the dividing wall (region 6), the column is provided with about 20 cm of the same packing. The feed e was fed in liquid form into the middle of the dividing wall region, and pre-evaporation was dispensed with.

The liquid sidestream takeoff f in the withdrawal section is at the same height. Above the dividing wall, the effluent liquid is combined in a collector and divided between the feed and the withdrawal side of the dividing wall by a swiveling funnel mounted within the column. The division ratio of liquid between feed and withdrawal side is advantageously from 1:4 to 1:4.5. The withdrawal rate of the sidestream is controlled via the column bottom fill level. An additional temperature control of the internal column temperature measured directly below the sidestream takeoff in the region 5 prevents, especially in the case of non-steady-state operating states such as starting-up and running-down procedures, the discharge of off-spec side effluents. Typically, a temperature of around 80.5° C. is observed at the side effluent takeoff.

The internal column temperature in the upper half of the common column region 1 is set to between 47° C. and 49° C. by a closed-loop temperature-controlled reflux rate (stream i). The column is equipped with a condenser K which is operated at about 5° C.

The column is equipped with a rotary film evaporator (4.6 $dm^2$) which is charged via a pump. Water and/or aqueous glyoxal solution (stream m) may be metered into its feed under car control. The high boiler fraction g' is removed under closed-loop temperature control at about 92° C. in the column bottom. Bottom and top effluent (streams g' and i' respectively) of the distillation column are recycled into the reservoir vessel B1. The entire column is equipped with adiabatic protective heaters.

EXAMPLE 418 g of a 40.7% glyoxal solution which contains, inter alia, 1% of ethylene glycol, and also 324 g of distilled water (stream m) are metered within 24 hours into the bottom evaporator V of the dividing wall column. Bottom and top effluent (streams g' and i' respectively) of the distillation column are recycled into the reservoir vessel B1. An amount of 30 g is discharged at the high boiler stream g within 24 hours, which is necessary in order to restrict accumulation of high boilers. The 371 g amount of methanol consumed by the reaction is metered under level control into the reservoir vessel B1 (stream a). Several days of continuous operation beforehand ensure steady-state conditions in the laboratory apparatus. The effluents obtained are analyzed by gas chromatography and the content of glyoxal is determined titrimetrically.

Under the above-described process conditions, 1045 g of an aqueous TME solution are obtained at the sidestream takeoff f of the dividing wall column and contain, in addition to 37.6% by weight of 1,1,2,2-tetramethoxyethane, traces of methanol and other secondary components, also 0.15% of 2,3-dimethoxy-1,4-dioxane. This results in molar yields of 89% of theory based on glyoxal and 91% based on methanol.

Analysis of a sample of the feed stream e to the dividing wall column reveals, in addition to methanol, among other components, 12.4% by weight of 1,1,2,2-tetramethoxyethane, 8.2% of water, 3.2% of dimethoxydioxane and 1% of glyoxal. Analysis of a sample of the low boiler effluent i' reveals 99.5% by weight of methanol and, in addition to 0.2% of water, traces of other low boilers. In the discharged high boiler stream g, among other components, 26% by weight of glyoxal dimethyl acetal, 24% by weight of glyoxal, 20% by weight of water, 11.6% by weight of dimethoxydioxane and, in addition to traces of 1,1,2,2-tetramethoxyethane, also other high boilers of which some are unknown.

In a further laboratory column which is to be operated continuously, is equipped with approx. 1.80 m of a laboratory fabric packing of specific surface area 950 m$^2$/m$^3$ and has an internal diameter of 40 mm, the collected side effluents of the dividing wall column are subjected to an azeotroping agent distillation at 500 mbar. This column too is equipped with an oil-heated rotary film evaporator (4.6 dm$^2$) and equipped with adiabatic protective heaters.

The feed is introduced in such a way that the stripping section of this column has a length of 80 cm.

Methylcyclohexane is used as an auxiliary. The water-containing vapors withdrawn at the top of the column are introduced into a phase separator after condensation. The organic phase is fed back to the columns as reflux and the heavier aqueous phase is removed. The pure 1,1,2,2-tetramethoxyethane is obtained at the bottom by closed-loop fill level control. The purity of the product is ensured by closed-loop temperature control in the lower section of the column which acts on the evaporator heating. Typically, the bottom temperature is 135° C., while 61° C. are measured at the top of the column. The effluents are analyzed by gas chromatography.

For example, 2921 g of 99.3% by weight pure 1,1,2,2-tetramethoxyethane which, in addition to 0.6% by weight of 2,3-dimethoxy-1,4-dioxane, contains only traces of water and other components are obtained within 53 hours from 8032 g of an aqueous solution which contains 37.2% by weight of 1,1,2,2-tetramethoxyethane and 0.2% by weight of dimethoxydioxane. In the aqueous top effluent, in addition to a small amount of methanol (<0.1% by weight), traces of methylcyclohexane and 220 ppm of glyoxal dimethyl acetal can be detected.

In a further apparatus which consists substantially of a heatable jacketed tube of length 4 m which is charged with 250 ml of catalyst (LEWATIT® K2629), a portion of the aqueous top effluent obtained above is further treated. Filters are again mounted at the inlet and outlet of this reactor, in order to prevent discharge of the catalyst.

62 ml/h of the aqueous discharge are continuously pumped through the catalyst bed at ambient pressure. At an average reactor temperature of 70° C., the glyoxal dimethyl acetal content could be depleted to values of <10 ppm, which corresponds to the limit of detection of the gas chromatography used.

We claim:

1. A process for distillatively working up an aqueous composition which comprises 1,1,2,2-tetramethoxyethane, glyoxal dimethyl acetal and methanol, wherein the composition is worked up to form at least one low boiler fraction, at least one medium boiler fraction and at least one high boiler fraction in a dividing wall column in which a dividing wall is arranged in the longitudinal direction of the column to form an upper common column region, a lower common column region, a feed section having rectifying section and stripping section and a withdrawal section having rectifying section and stripping section, the dividing wall is arranged between the upper and the lower common column region and the aqueous composition is fed to the middle region of the feed section, and at least one medium boiler fraction comprising aqueous 1,1,2,2-tetramethoxyathane is obtained as a sidestream from the middle region of the withdrawal section, at least one high boiler fraction comprising glyoxal dimethyl acetal from the lower common column region and at least one low boiler fraction comprising methanol from the upper common column region.

2. A process as claimed in claim 1, wherein
the upper common subregion has from 5 to 50% of the total number of theoretical plates of the dividing wall column,
the rectifying section of the feed section has from 5 to 50% of the total number of theoretical plates of the dividing wall column,
the stripping section of the feed section has from 5 to 50% of the total number of theoretical plates of the dividing wall column,
the stripping section of the withdrawal section has from 5 to 50% of the total number of theoretical plates of the dividing wall column,
the rectifying section of the withdrawal section has from 5 to 50% of the total number of theoretical plates of the dividing wall column, and
the lower common section has from 5 to 50% of the total number of theoretical plates of the dividing wall column,
the total number of theoretical dividing wall plates of the dividing wall column being 100%.

3. A process as claimed in claim 1, wherein at least one high boiler fraction is obtained as a liquid sidestream in the lower section of the column from 1 to 5 theoretical plates above the column bottom and comprises glyoxal diniethyl acetal.

4. A process as claimed in claim 1, wherein glyoxal dimethyl acetal is isolated from at least one high boiler takeoff of the dividing wall column.

5. A process as claimed in claim 1, wherein the medium boiler fraction is withdrawn in liquid or gaseous form at the sidestream takeoff point and comprises 1,1,2,2-tetramethoxyethane.

6. A process as claimed in claim 1, wherein the aqueous composition has one or more of the following contents whose sum does not exceed 100% by weight:
from 8 to 28% by weight of 1,1,2,2-tetramethoxyethane
from 2 to 12% by weight of glyoxal dimethyl acetal
from 40 to 80% by weight of methanol
from 5 to 18% by weight of water.

7. A process as claimed in claim 1, wherein the aqueous composition is obtained by reacting from 40 to 75% by weight aqueous glyoxal with methanol in the presence of an acidic catalyst, by leaving a liquid mixture which, at the start of the reaction, contains methanol and glyoxal in a molar ratio of at least 15:1 and water in a concentration of not more than 8% by weight in contact with the acidic catalyst until the concentration of the 1,1,2,2-tetramethoxyethane formed in the reaction mixture has reached at least 70% of the equilibrium concentration without more than 5% by weight of the methanol having been distilled off beforehand.

8. A process as claimed In claim 1, wherein the aqueous composition is obtained in the preparation of glyoxal monoacetals of the general formula (I)

by, in the process, reacting a mixture of from 20 to 60% by weight of aqueous glyoxal and glyoxal bisacetals of the general formula (II), in the presence of an acidic catalyst with a excess of a monohydric alcohol ROH until the reaction equilibrium has been attained.

9. A process as claimed in claim 1, wherein the liquid or gaseous aqueous side effluent of the dividing wall column, which contains most of the 1,1,2,2-tetramethoxyethane, is fed into a further column which is equipped with trays, structural packings or random packings and in which the water is removed with the aid of an azeotroping agent by distillation.

10. A process as claimed in claim 9, wherein the 1,1,2,2-tetramethoxyethane is at least partly obtained as a liquid or gaseous sidestream in the lower section of the column, and/or the bottom takeoff of this column is fed into the feed point of the dividing wall column.

11. A process for distillatively working up an aqueous composition which comprises 1,1,2,2-teiramethoxyethane, glyoxal dimethyl acetal and methanol, which comprises carrying out the workup of the composition according to the process as defined in claim 1 in a combination of two distillation columns in the form of a thermal coupling, which corresponds to the dividing wall column.

12. A process as claimed in claim 2, wherein at least one high boiler fraction is obtained as a liquid sidestream in the lower section of the column from 1 to 5 theoretical plates above the column bottom and comprises glyoxal dimethyl acetal.

13. A process as claimed in claim 2, wherein glyoxal dimethyl acetal is isolated from at least one high boiler takeoff of the dividing wall column.

14. A process as claimed in claim 3, wherein glyoxal dimethyl acetal is isolated from at least one high boiler takeoff of the dividing wall column.

15. A process as claimed in claim 2, wherein the medium boiler fraction is withdrawn in liquid or gaseous form at the sidestream takeoff point and comprises 1,1,2,2-tetramethoxyethane.

16. A process as claimed in claim 3, wherein the medium boiler fraction is withdrawn in liquid or gaseous form at the sidestream takeoff point and comprises 1,1,2,2-tetramethoxyethane.

17. A process as claimed in claim 4, wherein the medium boiler fraction is withdrawn in liquid or gaseous form at the sidestream takeoff point and comprises 1,1,2,2-teiramethoxyethane.

18. A process as claimed in claim 2, wherein the aqueous composition has one or more of the following contents whose sum does not exceed 100% by weight:
from 8 to 28% by weight of 1,1,2,2-tetramethoxyethane
from 2 to 12% by weight of glyoxal dimethyl acetal
from 40 to 80% by weight of methanol
from 5 to 18%by weight of water.

19. A process as claimed in claim 3, wherein the aqueous composition has one or more of the following contents whose sum does not exceed 100% by weight:
from 8 to 28% by weight of 1,1,2,2-tetramethoxyethane
from 2 to 12% by weight of glyoxal dimethyl acetal
from 40 to 80% by weight of methanol
from 5 to 18% by weight of water.

20. A process as claimed in claim 4, wherein the aqueous composition has one or more of the following contents whose sum does not exceed 100% by weight:
from 8 to 28% by weight of 1,1,2,2-tetramethoxyethane
from 2 to 12% by weight of glyoxal dimethyl acetal
from 40 to 80% by weight of methanol
from 5 to 18% by weight of water.

21. A process as claimed in claim 10, wherein the 1,1,2,2-tetramethoxyethane is at least partly obtained as a liquid or gaseous sidestream in the lower section of the column from 1 to 5 theoretical plates above the column bottom.

* * * * *